United States Patent [19]

Lauks

[11] Patent Number: 4,933,048
[45] Date of Patent: Jun. 12, 1990

[54] REFERENCE ELECTRODE, METHOD OF MAKING AND METHOD OF USING SAME

[75] Inventor: Imants R. Lauks, Morrisville, Pa.
[73] Assignee: I-Stat Corporation, Princeton, N.J.
[21] Appl. No.: 156,262
[22] Filed: Feb. 16, 1988
[51] Int. Cl.$^5$ ............................................. G01N 27/46
[52] U.S. Cl. .................................. 204/1.11; 204/400;
   204/416; 204/435; 427/58; 427/118; 427/125;
                                                   427/126.1
[58] Field of Search ................ 204/1 T, 400, 416-419,
                                  204/435; 427/58, 118, 125, 126.1

[56] References Cited

U.S. PATENT DOCUMENTS

| | | | |
|---|---|---|---|
| 3,591,482 | 7/1971 | Neff et al. | 204/435 |
| 4,053,382 | 10/1977 | Maruyama et al. | 204/435 |
| 4,166,021 | 8/1979 | Ross et al. | 204/435 |
| 4,214,968 | 7/1980 | Battaglia et al. | 204/435 |
| 4,454,007 | 6/1984 | Pace | 204/435 |

OTHER PUBLICATIONS

Sinsabaugh et al., "A Batch-Processed Reference Micro Electrode Integrated on a Silicon Substrate", from the Proceedings of the Symposium on electrochemical Sensors for Biomedical Applications (1986).

Primary Examiner—T. Tung
Attorney, Agent, or Firm—Pennie & Edmonds

[57] ABSTRACT

An improved reference electrode is disclosed for use in potentiometric measurements of the amount of ions in an aqueous solution. The reference electrode illustratively comprises a metal member on a substrate, and a layer of a salt reversible to the ion X overlying the metal member. The reference electrode is overlaid by a quantity of an electrolyte, which may be a polymer gel having a salt including the ion X dispersed therein. This structure is overlaid by a membrane permeable to water but not to the ion X that extends beyond the portion of the electrolyte overlying the electrode, but leaves a portion of the electrolyte exposed. This assembly may be shipped dry. In use, when the electrode is disposed in an aqueous solution containing an ionic species to be measured, water permeates the membrane and "wets up" the electrolyte relatively quickly. Any changes in ionic concentration, however, have to be made over a substantially longer path through the electrolyte between the electrode and the exposed portion such that the transit time for such changes is substantially longer than the wet-up time of the electrolyte. This reference electrode may be used in combination with a wide variety of potentiometric indicating electrodes or other structures.

14 Claims, 3 Drawing Sheets

REFERENCE ELECTRODE, METHOD OF MAKING AND METHOD OF USING SAME

FIELD OF THE INVENTION

This invention relates to an improved reference electrode. The reference electrode may be shipped "dry" and may be rapidly "wet-up" upon exposure to an aqueous solution.

BACKGROUND OF THE INVENTION

Typical devices for measuring the ionic content of solutions include a reference electrode and a separate potentiometric or "working" electrode. When these are immersed in a volume of solution to be analyzed, the reference and working electrodes together constitute an electrochemical cell. The reference electrode provides a constant potential with respect to which is measured the potential developed by the working electrode from the solution. The potential difference across the cell is proportional to the logarithm of the activity of the ion. This in turn is related to the concentration of the ion in the solution, such that the concentration can be directly determined as a function of the voltage measured across the reference and working electrodes.

Many documents discuss designs for and methods for fabrication of ion-sensitive devices for measuring the ionic content of solutions. For example, U.S. Pat. No. 4,613,442 issued to the present inventor shows an "Ambient Sensing Device" suitable for use at high temperatures. Other documents include European Patent Application 129,233 to Salman et al.; "A Batch-Processed Reference Micro Electrode Integrated on a Silicon Substrate", Sinsabaugh et al., in *Electrochemical Sensors for Biomedical Applications*, pp. 66-73 (1986); "Characteristics of Reference Electrodes Using a Polymer Gate ISFET", Matsuo et al., in *Sensors and Actuators*, 5 (1984), pp. 293-305; "An Integrated Sensor for Electrochemical Measurements", Smith et al., in *IEEE Transactions on Biomedical Engineering*, Vol. BME-33, No. 2, (1986) pp. 83-90; U.S. Pat. No. 4,592,824 to Smith et al., the disclosure of which appears to be comparable to that of the Smith et al. paper; "§3.7. Reference ISFET," in "Chemically Sensitive Field Effect Transistors"; Janata et al., in *Ion-Selective Electrodes in Analytical Chemistry*, vol. 2, (1980), pp. 161-167; *Ion-Selective Electrode Methodology*, vol. 1, (Covington ed.), pp. 58-62 (1979); *Ion-Selective Electrodes in Analytical Chemistry*, vol. 1, (Freiser ed.), especially chapter 3.3, "Reference Electrodes", pp. 323-331 (1978); and U.S. Pat. Nos. 4,437,969 to Covington et al. and 4,214,968 to Battaglia et al. See also "Chemically Sensitive Potentiometric Microsensors", by the present inventor, Stanford Research Institute (1983), pp. 192-241.

Typical reference electrodes comprise a layer of a material reversible to an ion X, that is, a material which is capable of undergoing a reversible change in oxidation state in response to the relative presence or absence of the ion X. Such materials include metal-halide salts, alloys or compounds. Conveniently this material is formed on the surface of an underlying metallic member. This reference electrode is then overlaid by an electrolyte. The electrolyte illustratively contains a quantity of the ion X dispersed into an aqueous medium, or into a polymeric material. For example, the electrolyte may comprise a gel containing a compound including the ion X. The gel is essentially impervious to mixing with the solution to be analyzed while permitting ion transport therethrough by diffusion. Alternatively the electrolyte may be confined behind a membrane, e.g. cellulose acetate or a porous glass or ceramic or the like, which permits ion transport while restraining flow of the solution and the electrolyte itself. A "liquid junction" is thus formed between the electrolyte and the test solution, which allows flow of ions by diffusion but not by convection.

When the composition of the electrolyte phase is suitably adjusted so that it contains ions at relatively high concentrations of closely similar mobilities, these ions traverse the liquid junction boundary in such a way as to provide electrical continuity between the electrode and the test solution (as required to perform the potentiometric measurement) and maintain a constant (and small) potential difference across the liquid junction boundary, regardless of the composition of the test solution. The potential difference between the electrode reversible to an ion X and its contacting electrolyte depends on the concentration of ion X in this electrolyte. Therefore, when ion X is at a constant concentration, the electrode potential of this electrode is independent of the composition of the solution contacting the liquid junction, which is the requirement for it to be a properly functioning reference electrode. Since ions must freely transport across the liquid junction boundary, constancy of ion X concentration can only be maintained if the electrolyte is a relatively large reservoir for ion X so that ion concentration in the electrolyte remains substantially constant over the time the reference electrode is in use.

Prior art macro-reference electrodes typically consist of a silver chloride coated silver wire dipped into a concentrated potassium chloride solution (or some equivalent formulation) contained in a tubular sleeve typically one-half inch in diameter by a few inches long. The volume of the electrolyte reservoir is several cm$^3$.

In a typical operational arrangement, the working and reference electrodes are sequentially exposed to, for example, a blood sample and a reagent containing a known concentration of the ions to be measured. By comparison of the potential difference between the reference and working electrodes responsive to the sample and the reagent, an accurately calibrated value can be determined for the concentration of the ion in the blood.

In order to provide a reference electrode which is useful in numerous processes, e.g. for blood analysis operations in hospitals, blood chemistry labs and the like, it is desirable to provide an electrode which is inexpensive, so as to be economically disposable, which is small, to allow use with small samples, and which has a long shelf life. The fact that most prior electrodes have employed hydrophilic or aqueous reference electrolytes make the long shelf life goal particularly difficult to achieve. Typically hydrophilic electrolytes have been hydrated gels or the like to allow ion transport. To ship and store such "wet" electrolytes involves a relatively complex packaging and storage problem. Alternatively the gels can be shipped dry and be hydrated prior to use, but this can cause further operational problems to arise, in particular, because of the size of such dry electrodes, the time it takes to properly hydrate them for use would significantly detract from their usability. A further difficulty is the physical size of prior art reference electrodes.

SUMMARY OF THE INVENTION

Accordingly, it is an object of the invention to provide a reference electrode structure which can be shipped dry, thus providing a long shelf life, but which can be "wet-up" for use relatively quickly thus maximizing convenience to the user.

It is a further object of the invention to provide such a sensor which can be manufactured using electronic circuit fabrication techniques such that it can be readily miniaturized for use in connection with miniature instruments and other demanding applications.

A reference electrode assembly according to a preferred embodiment of the invention comprises a metallic member which is coated with an electrode material reversible to an ion X and a layer of an electrolyte containing ion X formed over the electrode. Typically the electrolyte may comprise a hydrophilic gel. A portion of the electrolyte extending beyond the perimeter of the electrode is overlaid by a membrane which is permeable to $H_2O$ molecules but not permeable to ion X. The membrane may be formed, for example, of polyvinylchloride (PVC) or polytetrafluoroethylene (PTFE) plastics, or silicone rubber. The thickness of the electrolyte layer under this permeable membrane is relatively thin, such that the distance through the electrolyte between the membrane and the electrode is relatively short. A portion of the electrolyte extends through the permeable membrane or is otherwise enabled to form a liquid junction with the solution at a position relatively distant from the electrode. Accordingly, the ions must diffuse along a relatively long path through the electrolyte between the liquid junction and the electrode. This provides a long time constant for ion diffusion, while the electrolyte may be "wet-up" relatively quickly. As a result, there is a period of time after the electrolyte is wet-up and before ion diffusion affects ionic concentrations in the vicinity of the electrode during which the potential at the electrode is substantially constant. This time period is sufficient for the working electrode to take good measurements of ionic concentrations in the test solution.

BRIEF DESCRIPTION OF THE DRAWINGS

The invention will be better understood if reference is made to the accompanying drawings, in which:

FIGS. 3(a) through 3(e), shows successive steps in the fabrication of the electrode of FIG. 2.

DESCRIPTION OF THE PREFERRED EMBODIMENTS

Figure 1:
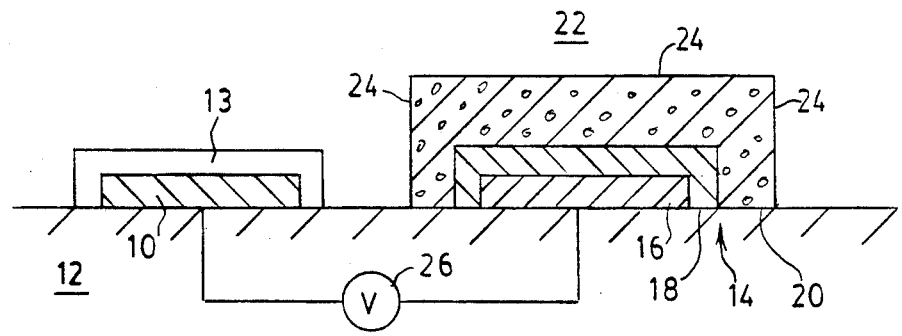
FIG. 1 shows a schematic cross-sectional view of a conventional prior art working electrode/reference electrode combination.

FIG. 1 shows a conventional working electrode/reference electrode assembly combination as employed in the prior art. A working electrode 10 is formed on a substrate 12 and covered with an overlayer 13. The overlayer 13 is a membrane or series of membranes that render the working electrode specific to a species to be measured. The working electrode may take numerous forms depending on its application. For example, it may be made of a metal such as silver and may include more complex structures consisting of a metal with overlayers of an electrolyte, an ion sensitive membrane, an enzyme layer or the like.

A reference electrode 14 is also formed on substrate 12. Reference electrode 14 comprises a metallic member 16, overcoated with a layer 18 that is overcoated in turn with an electrolyte layer 20. Layer 18 is made of a material reversible to an ion X, that is, a material which undergoes rapid exchange of ion X between it and the electrolyte so as to maintain thermodynamic equilibrium between it and the electrolyte, resulting in a constant electrical potential difference at constant concentrations of ion X.

Typical materials for layer 18 include suitable formulations or compounds (e.g. salts) including the ion X. Hereinafter reference to a "salt" layer should be understood to refer to a layer of such a reversible material. Electrolyte 20 may typically comprise a hydrophilic binder, such as a gel, having a salt in solid solution therein. One ion of the latter salt may be common to the salt of the salt layer 18. Illustratively, the metallic member is silver, layer 18 is silver chloride and the electrolyte is a gel containing potassium chloride.

In operation electrolyte 20 is permeated by water molecules from an aqueous solution 22 whose chemical concentration is to be measured by the working electrode. That is, the electrolyte 20 is selected to allow diffusion of water molecules as well as the ionic species in the water, but the electrolyte 20 does not allow convection, that is, flow of liquid water therethrough. Ionic species present in the electrolyte will also diffuse through the electrolyte into the aqueous solution. The junction 24 between the electrolyte 20 and the solution 22 is generally referred to as a "liquid junction."

As described generally above, the working electrode 10 and the reference electrode 14 together comprise an electrochemical cell. The potential between them (measured as indicated schematically by a voltmeter 26) may be used to derive a value for the concentration of the ionic species to be measured in the solution 22.

It can be seen from FIG. 1 that the volume of electrolyte 20 in the reference electrode assembly is relatively great. This is to insure that it takes some time for changes to occur in the concentration of the ionic species in the electrolyte as a result of diffusion through the electrolyte as the concentration in the electrolyte seeks equilibrium with that in the solution 22. In this way the potential difference between the reference electrode 14 and the working electrode 10 will remain constant for some time, permitting a measurement to be made of the ionic concentration in the solution 22.

However, the requirement that the volume of the electrolyte be relatively great, and that it be wet, places certain significant constraints on its use. For example, if the electrolyte is to be shipped dry and is to be "wet-up" prior to use by immersion in water or a salt solution, the time required is commensurate with the time constant of the ion-diffusion process, which is an impediment to the convenient use of such electrodes. On the other hand, if the electrodes are shipped wet then they must be stored wet, which is clumsy and inconvenient as well. Nor would it be possible, according to the teachings of the prior art, simply to reduce the volume of the electrolyte 20 so that it would "wet-up" more quickly; this would also reduce the time required for the ionic concentration in the electrolyte to reach equilibrium with that of the solution 22 under test, which would render the measurement itself difficult if not impossible.

The present invention provides a reference electrode assembly which can be shipped and stored dry, for convenience and long shelf life, and which provides a suitably long ion diffusion time constant but which can "wet-up" quickly.

Figure 2:
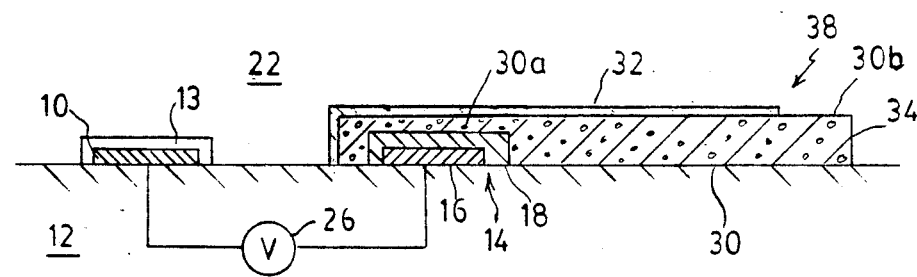
FIG. 2 shows a view comparable to FIG. 1, but showing a first embodiment of a working electrode/reference electrode assembly according to the present invention.

A preferred embodiment of the inventive reference electrode assembly is shown in FIG. 2. A working electrode 10 and a reference electrode assembly 38 are formed on a substrate 12 as in the prior art electrode of FIG. 1. The materials of the working electrode 10 and of reference electrode 14, that is, the metal layer 16 and the overlying salt layer 18, may be the same as in the device of the FIG. 1, and of course their connection to the voltmeter 26 is the same. The material of the electrolyte layer 30 can also be the same as that of electrolyte layer 20 of FIG. 1. As in the case of FIG. 1, layer 18 of FIG. 2 is made of a material that undergoes rapid exchange of an ion X between it and electrolyte layer 30.

According to the invention, a portion of the electrolyte layer 30a extending beyond layers 16 and 18 is covered by a membrane 32. Membrane 32 comprises a permselective material which is selectively permeable to water ($H_2O$) molecules but is impermeable to the ion X and, in general, is impermeable to any ion present in electrolyte 30 or present in the solution in which the reference electrode is to be used which can affect the potential developed at electrode 14. Membrane 32 may be made of PVC or PTFE plastic materials or of silicone rubber. A second portion 30b of the electrolyte that is displaced from layers 16 and 18 may be exposed to the solution 22 directly, as shown. Accordingly, a liquid junction 34 is formed between the solution 22 and portion 30b of the electrolyte 30.

In practice, the electrode assembly shown in FIG. 2 is shipped dry, such that the electrolyte contains an insufficient amount of water to support ion diffusion. Such an assembly is stable and has a long shelf life. When the assembly is brought into contact with an aqueous solution 22, individual water molecules penetrate the permselective membrane 32 and wet up the electrolyte and both water molecules and ions X cross the liquid junction. Since the electrolyte layer 30 is relatively thin compared to its length, the electrolyte 30 "wets-up" relatively quickly. At the same time, ionic species in both the electrolyte and the water begins to diffuse across the liquid junction, with changes in the concentrations of these species moving at essentially constant rates from the exposed portion 30b of the electrolyte leftward in the diagram of FIG. 2. Since the water molecules "wet-up" the electrolyte layer over the much shorter distance of top to bottom in the layer, the electrolyte is fully "wet-up" prior to the time the ions diffusing from the solution 22 reach the vicinity of the electrode layers 16, 18. As a result, there is a substantial time lag between the time the electrolyte is fully "wet-up" and therefore operational and the time changes begin to appear in the concentration of the ions (and hence the electrode potential) in the region of the electrolyte adjacent the electrode because of diffusion of ions across the liquid junction. During this time lag, electric continuity is provided by ion transport across the liquid junction, but the electrode potential remains constant since the changes in ion concentration will not have reached the electrode. As a result, an accurate measurement can be made of ion concentration by measuring the potential difference between the working electrode and the reference electrode.

Figure 4:
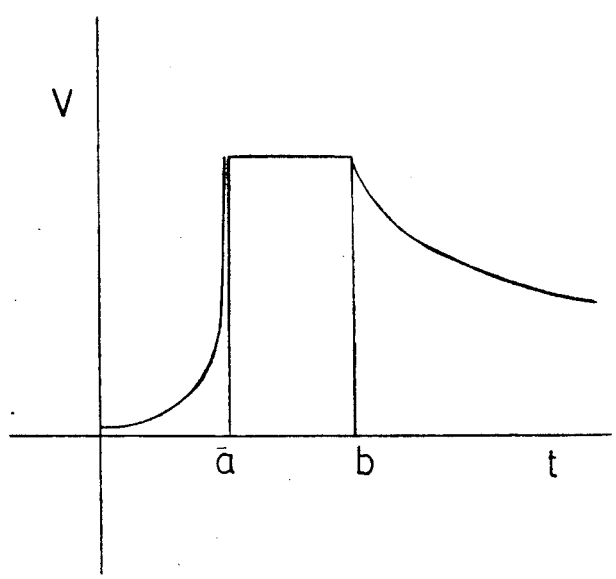
FIG. 4 is a diagram illustrating potential versus time useful in understanding the invention.

This performance of the reference electrode of FIG. 2 is illustrated in the plot of FIG. 4 of voltage against time. As shown therein, in the time period from 0 to a, the reference electrode wets-up and the voltage changes rapidly. In the period a-b, the voltage remains substantially constant until at time b the ionic concentration adjacent the electrode begins to change. In practice, time period a-b can be made to be a minute or more with reference electrodes of the present invention, which allows adequate time for the working electrode to make the necessary measurements.

Those of skill in the art will recognize that the reference electrode structure shown can be used in a number of different applications, and in a number of different experimental arrangements. Accordingly, disclosure herein of a particular method of use of the electrode assembly according to the invention should not be deemed to limit the invention thereto.

Figure 3:
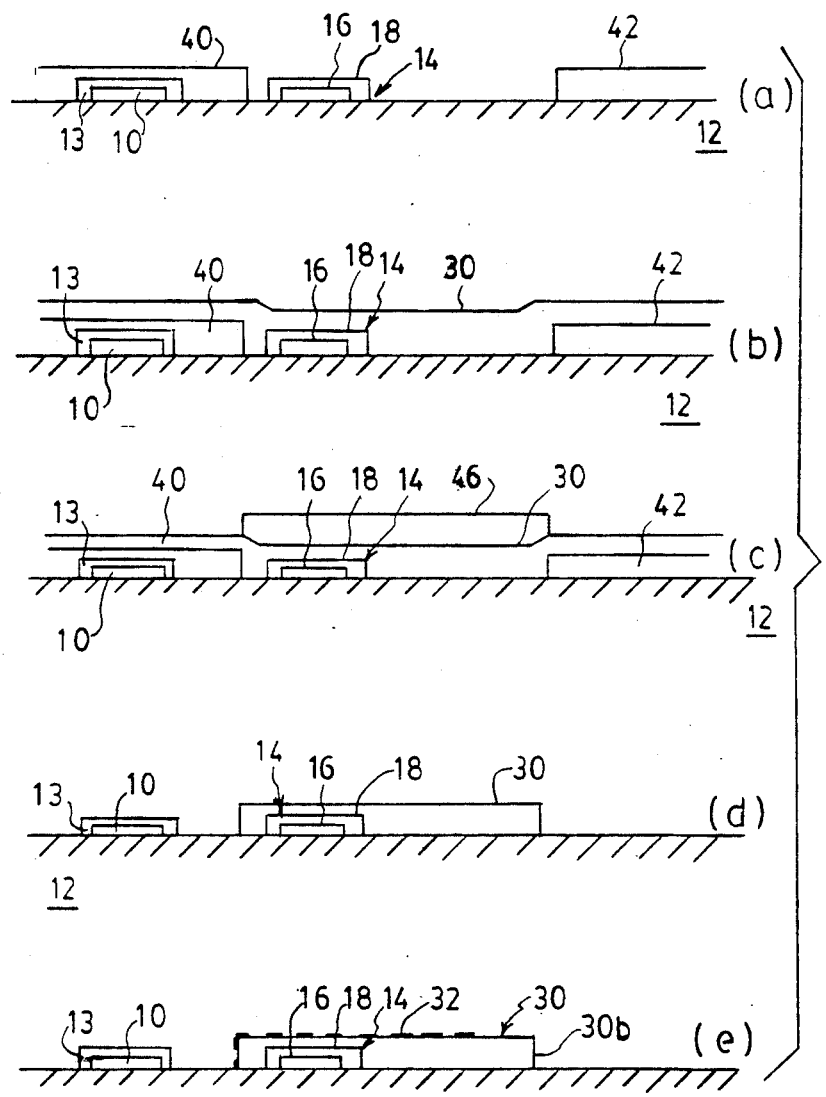
FIG. 3, comprising

FIGS. 3(a) through 3(e) disclose typical stages in the formation of the reference electrode assembly shown in FIG. 2. In FIG. 3(a) the working electrode 10, overlayer 13, the metal layer 16, the overlying salt layer 18 and patterned photoresist areas 40 and 42 have been deposited on the substrate 12. This photoresist is referred to as a "positive resist" so as to distinguish it from a "negative resist" used later. Essentially the two resists need to be separately removable.

In FIG. 3(b) the electrolyte material 30 is shown having been deposited over the entire assembly of FIG. 3(a). It will be appreciated by those of skill in the art that a polymer gel or other nonmetallic electrolyte material can readily be deposited by casting or the like over the entire surface of a substrate having a large number of reference electrodes and working electrodes, as well as other possible structures formed thereon. However, patterned layers of such electrolyte materials cannot be formed using the usual microcircuit fabrication techniques, that is, they are not suitable for sputtering, vapor disposition or other techniques used to depost metallic layers. According to one aspect of the invention, this difficulty is avoided.

In FIG. 3(c) there is shown a subsequent stage of fabrication of the device of the invention, in which a pattern 46 of a negative resist material, that is, which may be removed separately from the positive resist 42, is deposited over the areas in which the electrolyte material 30 is to be retained as part of the reference electrode assembly 38 according to the invention. That is, the negative resist material is deposited, exposed and developed, leaving behind patterns 46 over the areas in which the electrolyte 30 is to appear in the completed product.

In FIG. 3(d) the result of several subsequent steps are shown. These include a plasma etching or other step to remove the exposed electrolyte, leaving behind the portion disposed under the negative resist pattern 46 of FIG. 3(c). The positive and negative resists are then removed, leaving the electrode structure shown in FIG. 3d, in which the reference electrode 14 is covered by the electrolyte 30.

Finally, FIG. 3(e) shows the result of the last step, in which membrane 32 is added over the electrolyte 30, leaving a portion 30b of the electrolyte exposed as shown. As mentioned, the membrane 32 may be formed of PVC or PTFE plastics or of silicone rubber. Other suitable materials may appear to those skilled in the art.

In another embodiment of the invention, the membrane 32 could extend over the entire electrolyte 30, and holes sized to permit passage of ions as well as water could be formed, e.g. by laser perforation or otherwise, in the portion of the membrane 32 covering the portion 30b of the electrolyte disposed beyond the perimeter of the reference electrode 14.

In another embodiment of the invention, the electrolyte 30 is patterned in the form of a meander line or spiral with one end 30a over the electrode 14 and the other end 30b, exposed to the solution. Permeable membrane 32 covers the entirety of the meander line except at 30b. Thus, the distance for diffusion of ions laterally along the layer 30 can be made very large.

In view of the foregoing description other methods of fabrication of the working electrode/reference electrode assembly may occur to those of skill in the art.

While several preferred embodiments of the invention have been shown and described, it will be realized by those skilled in the art that others are possible as well. In each case, an important aspect of the invention is that prior to use the reference electrode, illustratively comprising a metal covered by a salt layer, is covered by a dry electrolyte. A path for water molecules to diffuse through the electrolyte to reach the reference electrode is provided which is shorter than any path by which changes in ion concentration can reach the reference electrode. In this way the electrolyte in the vicinity of the electrode "wets-up" more quickly than the changes in ion concentration reach the electrode.

It will be understood by those of skill in the art that the reference electrode assembly of the invention can be used in combination with a wide variety of additional electrodes, which may be termed "potentiometric indicating" or simply "working" electrodes. These may include electrodes which are actually ion-selective. The reference electrode of the invention may also be used in connection with other types of structures or devices.

Accordingly, while a number of preferred embodiments of the invention have been described, the invention is not to be limited thereby but only by the following claims.

What is claimed is:

1. A reference electrode assembly comprising:
   an electrode comprising an outer layer of a material reversible to a chemical species, said electrode being disposed on a substrate;
   a first layer of an electrolyte material covering all portions of said electrode not in contact with said substrate and extending beyond the perimeter of said electrode; and
   a second layer of material impermeable to said chemical species but permeable to water extending over a portion of said electrolyte layer beyond the perimeter of said electrode,
   such that when said electrode contacts an aqueous solution a first portion of the surface of the electrolyte over the electrode and extending beyond the perimeter of said electrode is contacted by water but is sealed with respect to said chemical species and a liquid junction is formed at a remaining exposed second portion of the surface of the electrolyte; and
   wherein the distance in the electrolyte between the exposed second portion of the surface of said electrolyte material and the electrode is large compared to the distance in the electrolyte between the impermeable layer and the electrode.

2. A reference electrode of claim 1 wherein said electrode is formed by thin film fabrication techniques.

3. The reference electrode assembly of claim 1 wherein said electrode is generally planar.

4. The reference electrode assembly of claim 1 wherein said electrode comprises a metal portion in contact with said substrate and said outer layer is of a salt or a compound of said metal which is reversible to said chemical species.

5. The reference electrode assembly of claim 4 wherein said chemical species is $Cl^-$, the metal portion is Ag and the overlying outer layer is AgCl.

6. The reference electrode assembly of claim 4 wherein said electrolyte is a material having KCl dispersed therein.

7. The reference electrode assembly of claim 1 wherein said second layer is formed of PVC, PTFE, or silicone rubber material.

8. In combination, a reference electrode assembly and a working electrode, the reference electrode assembly comprising:
   an electrode having an outer layer of a material reversible to a chemical species, said electrode being disposed on a substrate;
   a first layer of an electrolyte material covering all portions of said electrode not in contact with said substrate and extending beyond the perimeter of said electrode; and
   a second layer of material impermeable to said chemical species but permeable to water extending over a portion of said electrolyte layer beyond the perimeter of said electrode,
   such that when said electrode contacts an aqueous solution a first portion of the surface of the electrolyte over the electrode and extending beyond the perimeter of said electrode is contacted by water but is sealed with respect to said chemical species and a liquid junction is formed at a remaining exposed second portion of the surface of the electrolyte, and such that the distance in the electrolyte between the exposed second portion of the surface of said electrolyte material and the electrode is large compared to the distance in the electrolyte between the impermeable layer and the electrode.

9. The combination of claim 8 wherein said reference and working electrodes are formed on a common substrate.

10. The combination of claim 8 wherein said electrodes are formed using thin film fabrication techniques.

11. A reference electrode assembly comprising:
    an electrode comprising an outer layer of a material reversible to a chemical species, said electrode being disposed on a substrate;
    a first layer of an electrolyte material covering all portions of said electrode not in contact with said substrate and extending beyond the perimeter of said electrode; and
    a second layer of material permeable to water but impermeable to any chemical species present in said electrolyte material or in a solution in which the reference electrode is used whose concentration affects a potential developed at said electrode, said second layer extending over a portion of said electrolyte layer extending beyond the perimeter of said electrode,
    such that when said electrode contacts an aqueous solution a first portion of the surface of the electrolyte over the electrode and extending beyond the perimeter of said electrode is contacted by water but is sealed with respect to said chemical species and a liquid junction is formed at a remaining exposed second portion of the surface of the electrolyte; and wherein the distance in the electrolyte between the exposed second portion of the surface of said electrolyte material and the electrode is large compared to the distance in the electrolyte between the impermeable layer and the electrode.

12. A method for measuring a signal responsive to the concentration of an chemical species in an aqueous solution, comprising the steps of:

manufacturing a reference electrode assembly, said assembly comprising an electrode on a substrate, said electrode being surrounded by a dry electrolyte, a portion of said electrolyte extending over said electrode beyond the perimeter of said electrode being covered by a layer of material permeable to water and impermeable to any chemical species present in said solution or in said electrolyte whose concentration affects a potential developed at said electrode, another portion of said electrolyte being exposed, such that the distance in said electrolyte from said layer of material to said electrode is less than the distance in said electrolyte from the exposed portion of the electrolyte to the electrode;

assembling the reference electrode assembly together with a working electrode, and connecting said electrodes to means for measuring the voltage therebetween;

placing said reference electrode assembly and said working electrode in contact with an aqueous solution containing the chemical species whose concentration is to be measured, whereby the electrolyte wets-up faster than concentration changes takes place in the electrolyte as a result of migration between the exposed portion of the electrolyte and the electrode; and monitoring the potential difference between said reference and working electrodes.

13. The method of claim 12 comprising the further step of calibrating said assembly by exposure thereof to a reagent having a predetermined concentration of said chemical species.

14. A method of manufacture of a working electrode and reference electrode assembly, comprising the steps of:

depositing layers forming a working electrode and a conductor for a reference electrode on a substrate;

forming a layer of a material reversible to a chemical species over the conductor, thus forming a reference electrode;

depositing a layer of a dry electrolyte over said reference electrode; and forming a layer of a material permeable to water and impermeable to said chemical species over said layer of electrolyte, such that an exposed portion of said layer of electrolyte beyond the perimeter of the reference electrode is not covered by said layer of material;

wherein the distance through said electrolyte between said layer of material and said reference electrode is small compared to the distance through said electrolyte between the exposed portion of said electrolyte and said reference electrode.

* * * * *